(12) United States Patent
Aida et al.

(10) Patent No.: US 6,646,116 B1
(45) Date of Patent: Nov. 11, 2003

(54) VARIANT TAX GENE OF BOVINE LEUKEMIA VIRUS

(75) Inventors: Yoko Aida, 3-105, Sharera tsukuba matsushiro, 21-2, Matsushiro 4-chome, Tsukuba-shi, Ibaraki 305-0035 (JP); Shigeru Tajima, 203, Sanraifu nakane, 1-38-7, Kannondai, Tsukuba-shi Ibaraki 305-0856 (JP)

(73) Assignees: Riken, Saitama (JP); Yoko Aida, Ibaraki (JP); Shigeru Tajima, Ibaraki (JP)

( * ) Notice: Subject to any disclaimer, the term of this patent is extended or adjusted under 35 U.S.C. 154(b) by 0 days.

(21) Appl. No.: 09/415,260

(22) Filed: Oct. 12, 1999

(30) Foreign Application Priority Data

Mar. 31, 1999 (JP) ............................................ 11-091875

(51) Int. Cl.$^7$ ............................................... C07H 21/04
(52) U.S. Cl. .................................. 536/23.72; 424/207.1
(58) Field of Search .................... 536/23.72; 424/182.1, 424/207.1

(56) References Cited

PUBLICATIONS

PCR Technology – Principles and Applications for DNA Amplification, Stockton press, 1989, Henry A. Erlich, Editor, pp. ix, x, Part One – Basic Methology, pp. 1–5.*

Sagata et al., Proc. Natl. Acad. Sci. USA. vol. 81, pp. 4741–4745, 1984.

Kramer et al., Methods in Enzymology, vol. 154, Part E, pp. 350–367, 1987.

Tajima et al., Virology, 243, pp. 235–246, 1998.

Inabe et al., Virology, vol. 245, pp. 53–64, 1998.

* cited by examiner

*Primary Examiner*—Laurie Scheiner
*Assistant Examiner*—Jeffrey S. Parkin
(74) *Attorney, Agent, or Firm*—Greenblum & Bernstein, P.L.C.

(57) ABSTRACT

A variant tax gene of bovine leukemia virus enhancing ability to induce replication of bovine leukemia virus or a retrovirus related to the bovine leukemia virus which encodes a variant gene product containing one or more mutations selected from the group consisting of substitution of the 240th Ser for Thr, substitution of the 247th Asp for Gly, substitution of the 251st Thr for Ala, substitution of the 258th Asp for Gly, substitution of the 261st His for Arg, substitution of the 261st His for Tyr, and substitution of the 265th Ser for Gly.

1 Claim, 1 Drawing Sheet

```
  1  MASVVGWGPH SLHACPALVL SNDVTIDAWC PLCGPHERLQ FERIDTTLTC ETHRITWTAD  60
     ---------- ---------- ---------- ---------- ---------- ----------
     ---------- ---------- ---------- ---------- ---------- ----------
     ---------- ---------- ---------- ---------- ---------- ----------
     ---------- ---------- ---------- ---------- ---------- ----------
     ---------- ---------- ---------- ---------- ---------- ----------
     ---------- ---------- ---------- ---------- ---------- ----------
     ---------- ---------- ---------- ---------- ---------- ----------

61  GRPFGLNGTL FPRLHVSETR PQGPRRLWIN CPLPAVRAQP GPVSLSPFEQ SPFQPYQCQL 120
     ---------- ---------- ---------- ---------- ---------- ----------
     ---------- ---------- ---------- ---------- ---------- ----------
     ---------- ---------- ---------- ---------- ---------- ----------
     ---------- ---------- ---------- ---------- ---------- ----------
     ---------- ---------- ---------- ---------- ---------- ----------
     ---------- ---------- ---------- ---------- ---------- ----------
     ---------- ---------- ---------- ---------- ---------- ----------

121  PSASSDGCPI IGHGLLPWNN LVTHPVLGKV LILNQMANFS LLPPFDTLLV DPLRLSVFAP 180
     ---------- ---------- ---------- ---------- ---------- ----------
     ---------- ---------- ---------- ---------- ---------- ----------
     ---------- ---------- ---------- ---------- ---------- ----------
     ---------- ---------- ---------- ---------- ---------- ----------
     ---------- ---------- ---------- ---------- ---------- ----------
     ---------- ---------- ---------- ---------- ---------- ----------
     ---------- ---------- ---------- ---------- ---------- ----------
                                                                    ↓
181  DTRGAIRYLS TLLTLCPVTC ILPLGEPFSP NVPICRFPRD TSEPPLSEFE LPLIQTPGLS 240
     ---------- ---------- ---------- ---------- ---------- ---------T
     ---------- ---------- ---------- ---------- ---------- ----------
     ---------- ---------- ---------- ---------- ---------- ----------
     ---------- ---------- ---------- ---------- ---------- ----------
     ---------- ---------- ---------- ---------- ---------- ----------
     ---------- ---------- ---------- ---------- ---------- ----------
     ---------- ---------- ---------- ---------- ---------- ----------

↓         ↓    ↓ ↓
241  WSVPAIDLFL TGPPSPYDRL HVWSSPQALQ RFLHDPTLTW SELVASGKLR LDSPLKLQLL 300
     -------G-- ---------- ---------- ---------- ---------- ----------
     ---------- A--------- ---------- ---------- ---------- ----------
     ---------- -------G-- ---------- ---------- ---------- ----------
     ---------- ---------- R--------- ---------- ---------- ----------
     ---------- ---------- Y--------- ---------- ---------- ----------
     ---------- ---------- ----G----- ---------- ---------- ----------

301  ENEWLSRLF   WILD TYPE (SEQ ID NO:1)
     ---------    S240T  (SEQ ID NO:2)
     ---------    D247G  (SEQ ID NO:3)
     ---------    T251A  (SEQ ID NO:4)
     ---------    D258G  (SEQ ID NO:5)
     ---------    H261R  (SEQ ID NO:6)
     ---------    H261Y  (SEQ ID NO:7)
     ---------    S265G  (SEQ ID NO:8)
```

FIGURE 1

SEQUENCE LISTING

<160> NUMBER OF SEQ ID NOS: 10

<210> SEQ ID NO 1
<211> LENGTH: 309
<212> TYPE: PRT
<213> ORGANISM: Bovine leukemia virus

<400> SEQUENCE: 1

Met Ala Ser Val Val Gly Trp Gly Pro His Ser Leu His Ala Cys Pro
1               5                   10                  15

Ala Leu Val Leu Ser Asn Asp Val Thr Ile Asp Ala Trp Cys Pro Leu
            20                  25                  30

Cys Gly Pro His Glu Arg Leu Gln Phe Glu Arg Ile Asp Thr Thr Leu
        35                  40                  45

Thr Cys Glu Thr His Arg Ile Thr Trp Thr Ala Asp Gly Arg Pro Phe
    50                  55                  60

Gly Leu Asn Gly Thr Leu Phe Pro Arg Leu His Val Ser Glu Thr Arg
65                  70                  75                  80

Pro Gln Gly Pro Arg Arg Leu Trp Ile Asn Cys Pro Leu Pro Ala Val
                85                  90                  95

Arg Ala Gln Pro Gly Pro Val Ser Leu Ser Pro Phe Glu Gln Ser Pro
            100                 105                 110

Phe Gln Pro Tyr Gln Cys Gln Leu Pro Ser Ala Ser Ser Asp Gly Cys
        115                 120                 125

Pro Ile Ile Gly His Gly Leu Leu Pro Trp Asn Asn Leu Val Thr His
    130                 135                 140

Pro Val Leu Gly Lys Val Leu Ile Leu Asn Gln Met Ala Asn Phe Ser
145                 150                 155                 160

Leu Leu Pro Pro Phe Asp Thr Leu Leu Val Asp Pro Leu Arg Leu Ser
                165                 170                 175

Val Phe Ala Pro Asp Thr Arg Gly Ala Ile Arg Tyr Leu Ser Thr Leu
            180                 185                 190

Leu Thr Leu Cys Pro Val Thr Cys Ile Leu Pro Leu Gly Glu Pro Phe
        195                 200                 205

Ser Pro Asn Val Pro Ile Cys Arg Phe Pro Arg Asp Thr Ser Glu Pro
    210                 215                 220

Pro Leu Ser Glu Phe Glu Leu Pro Leu Ile Gln Thr Pro Gly Leu Ser
225                 230                 235                 240

Trp Ser Val Pro Ala Ile Asp Leu Phe Leu Thr Gly Pro Pro Ser Pro
                245                 250                 255

Tyr Asp Arg Leu His Val Trp Ser Ser Pro Gln Ala Leu Gln Arg Phe
            260                 265                 270

Leu His Asp Pro Thr Leu Thr Trp Ser Glu Leu Val Ala Ser Gly Lys
        275                 280                 285

Leu Arg Leu Asp Ser Pro Leu Lys Leu Gln Leu Glu Asn Glu Trp
    290                 295                 300

Leu Ser Arg Leu Phe
305

<210> SEQ ID NO 2
<211> LENGTH: 309
<212> TYPE: PRT
<213> ORGANISM: Bovine leukemia virus

<400> SEQUENCE: 2

-continued

```
Met Ala Ser Val Val Gly Trp Gly Pro His Ser Leu His Ala Cys Pro
1               5                   10                  15

Ala Leu Val Leu Ser Asn Asp Val Thr Ile Asp Ala Trp Cys Pro Leu
                20                  25                  30

Cys Gly Pro His Glu Arg Leu Gln Phe Glu Arg Ile Asp Thr Thr Leu
            35                  40                  45

Thr Cys Glu Thr His Arg Ile Thr Trp Thr Ala Asp Gly Arg Pro Phe
        50                  55                  60

Gly Leu Asn Gly Thr Leu Phe Pro Arg Leu His Val Ser Glu Thr Arg
65                  70                  75                  80

Pro Gln Gly Pro Arg Arg Leu Trp Ile Asn Cys Pro Leu Pro Ala Val
                85                  90                  95

Arg Ala Gln Pro Gly Pro Val Ser Leu Ser Pro Phe Glu Gln Ser Pro
            100                 105                 110

Phe Gln Pro Tyr Gln Cys Gln Leu Pro Ser Ala Ser Ser Asp Gly Cys
        115                 120                 125

Pro Ile Ile Gly His Gly Leu Leu Pro Trp Asn Asn Leu Val Thr His
    130                 135                 140

Pro Val Leu Gly Lys Val Leu Ile Leu Asn Gln Met Ala Asn Phe Ser
145                 150                 155                 160

Leu Leu Pro Pro Phe Asp Thr Leu Leu Val Asp Pro Leu Arg Leu Ser
                165                 170                 175

Val Phe Ala Pro Asp Thr Arg Gly Ala Ile Arg Tyr Leu Ser Thr Leu
            180                 185                 190

Leu Thr Leu Cys Pro Val Thr Cys Ile Leu Pro Leu Gly Glu Pro Phe
        195                 200                 205

Ser Pro Asn Val Pro Ile Cys Arg Phe Pro Arg Asp Thr Ser Glu Pro
    210                 215                 220

Pro Leu Ser Glu Phe Glu Leu Pro Leu Ile Gln Thr Pro Gly Leu Thr
225                 230                 235                 240

Trp Ser Val Pro Ala Ile Asp Leu Phe Leu Thr Gly Pro Pro Ser Pro
                245                 250                 255

Tyr Asp Arg Leu His Val Trp Ser Ser Pro Gln Ala Leu Gln Arg Phe
            260                 265                 270

Leu His Asp Pro Thr Leu Thr Trp Ser Glu Leu Val Ala Ser Gly Lys
        275                 280                 285

Leu Arg Leu Asp Ser Pro Leu Lys Leu Gln Leu Leu Glu Asn Glu Trp
    290                 295                 300

Leu Ser Arg Leu Phe
305
```

<210> SEQ ID NO 3
<211> LENGTH: 309
<212> TYPE: PRT
<213> ORGANISM: Bovine leukemia virus

<400> SEQUENCE: 3

```
Met Ala Ser Val Val Gly Trp Gly Pro His Ser Leu His Ala Cys Pro
1               5                   10                  15

Ala Leu Val Leu Ser Asn Asp Val Thr Ile Asp Ala Trp Cys Pro Leu
                20                  25                  30

Cys Gly Pro His Glu Arg Leu Gln Phe Glu Arg Ile Asp Thr Thr Leu
            35                  40                  45

Thr Cys Glu Thr His Arg Ile Thr Trp Thr Ala Asp Gly Arg Pro Phe
```

```
              50                  55                  60
Gly Leu Asn Gly Thr Leu Phe Pro Arg Leu His Val Ser Glu Thr Arg
 65                  70                  75                  80

Pro Gln Gly Pro Arg Arg Leu Trp Ile Asn Cys Pro Leu Pro Ala Val
                 85                  90                  95

Arg Ala Gln Pro Gly Pro Val Ser Leu Ser Pro Phe Glu Gln Ser Pro
                100                 105                 110

Phe Gln Pro Tyr Gln Cys Gln Leu Pro Ser Ala Ser Ser Asp Gly Cys
                115                 120                 125

Pro Ile Ile Gly His Gly Leu Leu Pro Trp Asn Asn Leu Val Thr His
                130                 135                 140

Pro Val Leu Gly Lys Val Leu Ile Leu Asn Gln Met Ala Asn Phe Ser
145                 150                 155                 160

Leu Leu Pro Pro Phe Asp Thr Leu Leu Val Asp Pro Leu Arg Leu Ser
                165                 170                 175

Val Phe Ala Pro Asp Thr Arg Gly Ala Ile Arg Tyr Leu Ser Thr Leu
                180                 185                 190

Leu Thr Leu Cys Pro Val Thr Cys Ile Leu Pro Leu Gly Glu Pro Phe
                195                 200                 205

Ser Pro Asn Val Pro Ile Cys Arg Phe Pro Arg Asp Thr Ser Glu Pro
                210                 215                 220

Pro Leu Ser Glu Phe Glu Leu Pro Leu Ile Gln Thr Pro Gly Leu Ser
225                 230                 235                 240

Trp Ser Val Pro Ala Ile Gly Leu Phe Leu Thr Gly Pro Pro Ser Pro
                245                 250                 255

Tyr Asp Arg Leu His Val Trp Ser Ser Pro Gln Ala Leu Gln Arg Phe
                260                 265                 270

Leu His Asp Pro Thr Leu Thr Trp Ser Glu Leu Val Ala Ser Gly Lys
                275                 280                 285

Leu Arg Leu Asp Ser Pro Leu Lys Leu Gln Leu Leu Glu Asn Glu Trp
                290                 295                 300

Leu Ser Arg Leu Phe
305

<210> SEQ ID NO 4
<211> LENGTH: 309
<212> TYPE: PRT
<213> ORGANISM: Bovine leukemia virus

<400> SEQUENCE: 4

Met Ala Ser Val Val Gly Trp Gly Pro His Ser Leu His Ala Cys Pro
 1                   5                  10                  15

Ala Leu Val Leu Ser Asn Asp Val Thr Ile Asp Ala Trp Cys Pro Leu
                 20                  25                  30

Cys Gly Pro His Glu Arg Leu Gln Phe Glu Arg Ile Asp Thr Thr Leu
                 35                  40                  45

Thr Cys Glu Thr His Arg Ile Thr Trp Thr Ala Asp Gly Arg Pro Phe
             50                  55                  60

Gly Leu Asn Gly Thr Leu Phe Pro Arg Leu His Val Ser Glu Thr Arg
 65                  70                  75                  80

Pro Gln Gly Pro Arg Arg Leu Trp Ile Asn Cys Pro Leu Pro Ala Val
                 85                  90                  95

Arg Ala Gln Pro Gly Pro Val Ser Leu Ser Pro Phe Glu Gln Ser Pro
                100                 105                 110
```

```
Phe Gln Pro Tyr Gln Cys Gln Leu Pro Ser Ala Ser Ser Asp Gly Cys
            115                 120                 125

Pro Ile Ile Gly His Gly Leu Leu Pro Trp Asn Asn Leu Val Thr His
        130                 135                 140

Pro Val Leu Gly Lys Val Leu Ile Leu Asn Gln Met Ala Asn Phe Ser
145                 150                 155                 160

Leu Leu Pro Pro Phe Asp Thr Leu Leu Val Asp Pro Leu Arg Leu Ser
                165                 170                 175

Val Phe Ala Pro Asp Thr Arg Gly Ala Ile Arg Tyr Leu Ser Thr Leu
            180                 185                 190

Leu Thr Leu Cys Pro Val Thr Cys Ile Leu Pro Leu Gly Glu Pro Phe
            195                 200                 205

Ser Pro Asn Val Pro Ile Cys Arg Phe Pro Arg Asp Thr Ser Glu Pro
        210                 215                 220

Pro Leu Ser Glu Phe Glu Leu Pro Leu Ile Gln Thr Pro Gly Leu Ser
225                 230                 235                 240

Trp Ser Val Pro Ala Ile Asp Leu Phe Leu Ala Gly Pro Pro Ser Pro
                245                 250                 255

Tyr Asp Arg Leu His Val Trp Ser Ser Pro Gln Ala Leu Gln Arg Phe
            260                 265                 270

Leu His Asp Pro Thr Leu Thr Trp Ser Glu Leu Val Ala Ser Gly Lys
            275                 280                 285

Leu Arg Leu Asp Ser Pro Leu Lys Leu Gln Leu Leu Glu Asn Glu Trp
            290                 295                 300

Leu Ser Arg Leu Phe
305

<210> SEQ ID NO 5
<211> LENGTH: 309
<212> TYPE: PRT
<213> ORGANISM: Bovine leukemia virus

<400> SEQUENCE: 5

Met Ala Ser Val Val Gly Trp Gly Pro His Ser Leu His Ala Cys Pro
1               5                   10                  15

Ala Leu Val Leu Ser Asn Asp Val Thr Ile Asp Ala Trp Cys Pro Leu
                20                  25                  30

Cys Gly Pro His Glu Arg Leu Gln Phe Glu Arg Ile Asp Thr Thr Leu
            35                  40                  45

Thr Cys Glu Thr His Arg Ile Thr Trp Thr Ala Asp Gly Arg Pro Phe
        50                  55                  60

Gly Leu Asn Gly Thr Leu Phe Pro Arg Leu His Val Ser Glu Thr Arg
65                  70                  75                  80

Pro Gln Gly Pro Arg Arg Leu Trp Ile Asn Cys Pro Leu Pro Ala Val
                85                  90                  95

Arg Ala Gln Pro Gly Pro Val Ser Leu Ser Pro Phe Glu Gln Ser Pro
            100                 105                 110

Phe Gln Pro Tyr Gln Cys Gln Leu Pro Ser Ala Ser Ser Asp Gly Cys
        115                 120                 125

Pro Ile Ile Gly His Gly Leu Leu Pro Trp Asn Asn Leu Val Thr His
    130                 135                 140

Pro Val Leu Gly Lys Val Leu Ile Leu Asn Gln Met Ala Asn Phe Ser
145                 150                 155                 160

Leu Leu Pro Pro Phe Asp Thr Leu Leu Val Asp Pro Leu Arg Leu Ser
                165                 170                 175
```

```
Val Phe Ala Pro Asp Thr Arg Gly Ala Ile Arg Tyr Leu Ser Thr Leu
            180                 185                 190

Leu Thr Leu Cys Pro Val Thr Cys Ile Leu Pro Leu Gly Glu Pro Phe
        195                 200                 205

Ser Pro Asn Val Pro Ile Cys Arg Phe Pro Arg Asp Thr Ser Glu Pro
    210                 215                 220

Pro Leu Ser Glu Phe Glu Leu Pro Leu Ile Gln Thr Pro Gly Leu Ser
225                 230                 235                 240

Trp Ser Val Pro Ala Ile Asp Leu Phe Leu Thr Gly Pro Pro Ser Pro
                245                 250                 255

Tyr Gly Arg Leu His Val Trp Ser Pro Gln Ala Leu Gln Arg Phe
            260                 265                 270

Leu His Asp Pro Thr Leu Thr Trp Ser Glu Leu Val Ala Ser Gly Lys
        275                 280                 285

Leu Arg Leu Asp Ser Pro Leu Lys Leu Gln Leu Leu Glu Asn Glu Trp
    290                 295                 300

Leu Ser Arg Leu Phe
305

<210> SEQ ID NO 6
<211> LENGTH: 309
<212> TYPE: PRT
<213> ORGANISM: Bovine leukemia virus

<400> SEQUENCE: 6

Met Ala Ser Val Val Gly Trp Gly Pro His Ser Leu His Ala Cys Pro
1               5                   10                  15

Ala Leu Val Leu Ser Asn Asp Val Thr Ile Asp Ala Trp Cys Pro Leu
            20                  25                  30

Cys Gly Pro His Glu Arg Leu Gln Phe Glu Arg Ile Asp Thr Thr Leu
        35                  40                  45

Thr Cys Glu Thr His Arg Ile Thr Trp Thr Ala Asp Gly Arg Pro Phe
    50                  55                  60

Gly Leu Asn Gly Thr Leu Phe Pro Arg Leu His Val Ser Glu Thr Arg
65                  70                  75                  80

Pro Gln Gly Pro Arg Arg Leu Trp Ile Asn Cys Pro Leu Pro Ala Val
                85                  90                  95

Arg Ala Gln Pro Gly Pro Val Ser Leu Ser Pro Phe Glu Gln Ser Pro
            100                 105                 110

Phe Gln Pro Tyr Gln Cys Gln Leu Pro Ser Ala Ser Ser Asp Gly Cys
        115                 120                 125

Pro Ile Ile Gly His Gly Leu Leu Pro Trp Asn Asn Leu Val Thr His
    130                 135                 140

Pro Val Leu Gly Lys Val Leu Ile Leu Asn Gln Met Ala Asn Phe Ser
145                 150                 155                 160

Leu Leu Pro Pro Phe Asp Thr Leu Leu Val Asp Pro Leu Arg Leu Ser
                165                 170                 175

Val Phe Ala Pro Asp Thr Arg Gly Ala Ile Arg Tyr Leu Ser Thr Leu
            180                 185                 190

Leu Thr Leu Cys Pro Val Thr Cys Ile Leu Pro Leu Gly Glu Pro Phe
        195                 200                 205

Ser Pro Asn Val Pro Ile Cys Arg Phe Pro Arg Asp Thr Ser Glu Pro
    210                 215                 220

Pro Leu Ser Glu Phe Glu Leu Pro Leu Ile Gln Thr Pro Gly Leu Ser
```

```
                225                 230                 235                 240

Trp Ser Val Pro Ala Ile Asp Leu Phe Leu Thr Gly Pro Pro Ser Pro
                245                 250                 255

Tyr Asp Arg Leu Arg Val Trp Ser Pro Gln Ala Leu Gln Arg Phe
            260                 265                 270

Leu His Asp Pro Thr Leu Thr Trp Ser Glu Leu Val Ala Ser Gly Lys
            275                 280                 285

Leu Arg Leu Asp Ser Pro Leu Lys Leu Gln Leu Leu Glu Asn Glu Trp
            290                 295                 300

Leu Ser Arg Leu Phe
305

<210> SEQ ID NO 7
<211> LENGTH: 309
<212> TYPE: PRT
<213> ORGANISM: Bovine leukemia virus

<400> SEQUENCE: 7

Met Ala Ser Val Val Gly Trp Gly Pro His Ser Leu His Ala Cys Pro
1               5                   10                  15

Ala Leu Val Leu Ser Asn Asp Val Thr Ile Asp Ala Trp Cys Pro Leu
            20                  25                  30

Cys Gly Pro His Glu Arg Leu Gln Phe Glu Arg Ile Asp Thr Thr Leu
        35                  40                  45

Thr Cys Glu Thr His Arg Ile Thr Trp Thr Ala Asp Gly Arg Pro Phe
    50                  55                  60

Gly Leu Asn Gly Thr Leu Phe Pro Arg Leu His Val Ser Glu Thr Arg
65                  70                  75                  80

Pro Gln Gly Pro Arg Arg Leu Trp Ile Asn Cys Pro Leu Pro Ala Val
                85                  90                  95

Arg Ala Gln Pro Gly Pro Val Ser Leu Ser Pro Phe Glu Gln Ser Pro
            100                 105                 110

Phe Gln Pro Tyr Gln Cys Gln Leu Pro Ser Ala Ser Ser Asp Gly Cys
        115                 120                 125

Pro Ile Ile Gly His Gly Leu Leu Pro Trp Asn Asn Leu Val Thr His
    130                 135                 140

Pro Val Leu Gly Lys Val Leu Ile Leu Asn Gln Met Ala Asn Phe Ser
145                 150                 155                 160

Leu Leu Pro Pro Phe Asp Thr Leu Leu Val Asp Pro Leu Arg Leu Ser
                165                 170                 175

Val Phe Ala Pro Asp Thr Arg Gly Ala Ile Arg Tyr Leu Ser Thr Leu
            180                 185                 190

Leu Thr Leu Cys Pro Val Thr Cys Ile Leu Pro Leu Gly Glu Pro Phe
        195                 200                 205

Ser Pro Asn Val Pro Ile Cys Arg Phe Pro Arg Asp Thr Ser Glu Pro
    210                 215                 220

Pro Leu Ser Glu Phe Glu Leu Pro Leu Ile Gln Thr Pro Gly Leu Ser
225                 230                 235                 240

Trp Ser Val Pro Ala Ile Asp Leu Phe Leu Thr Gly Pro Pro Ser Pro
                245                 250                 255

Tyr Asp Arg Leu Tyr Val Trp Ser Pro Gln Ala Leu Gln Arg Phe
            260                 265                 270

Leu His Asp Pro Thr Leu Thr Trp Ser Glu Leu Val Ala Ser Gly Lys
            275                 280                 285
```

```
Leu Arg Leu Asp Ser Pro Leu Lys Leu Gln Leu Leu Glu Asn Glu Trp
    290                 295                 300

Leu Ser Arg Leu Phe
305

<210> SEQ ID NO 8
<211> LENGTH: 309
<212> TYPE: PRT
<213> ORGANISM: Bovine leukemia virus

<400> SEQUENCE: 8

Met Ala Ser Val Val Gly Trp Gly Pro His Ser Leu His Ala Cys Pro
1               5                   10                  15

Ala Leu Val Leu Ser Asn Asp Val Thr Ile Asp Ala Trp Cys Pro Leu
            20                  25                  30

Cys Gly Pro His Glu Arg Leu Gln Phe Glu Arg Ile Asp Thr Thr Leu
        35                  40                  45

Thr Cys Glu Thr His Arg Ile Thr Trp Thr Ala Asp Gly Arg Pro Phe
    50                  55                  60

Gly Leu Asn Gly Thr Leu Phe Pro Arg Leu His Val Ser Glu Thr Arg
65                  70                  75                  80

Pro Gln Gly Pro Arg Arg Leu Trp Ile Asn Cys Pro Leu Pro Ala Val
                85                  90                  95

Arg Ala Gln Pro Gly Pro Val Ser Leu Ser Pro Phe Glu Gln Ser Pro
            100                 105                 110

Phe Gln Pro Tyr Gln Cys Gln Leu Pro Ser Ala Ser Ser Asp Gly Cys
        115                 120                 125

Pro Ile Ile Gly His Gly Leu Leu Pro Trp Asn Asn Leu Val Thr His
    130                 135                 140

Pro Val Leu Gly Lys Val Leu Ile Leu Asn Gln Met Ala Asn Phe Ser
145                 150                 155                 160

Leu Leu Pro Pro Phe Asp Thr Leu Leu Val Asp Pro Leu Arg Leu Ser
                165                 170                 175

Val Phe Ala Pro Asp Thr Arg Gly Ala Ile Arg Tyr Leu Ser Thr Leu
            180                 185                 190

Leu Thr Leu Cys Pro Val Thr Cys Ile Leu Pro Leu Gly Glu Pro Phe
        195                 200                 205

Ser Pro Asn Val Pro Ile Cys Arg Phe Pro Arg Asp Thr Ser Glu Pro
    210                 215                 220

Pro Leu Ser Glu Phe Glu Leu Pro Leu Ile Gln Thr Pro Gly Leu Ser
225                 230                 235                 240

Trp Ser Val Pro Ala Ile Asp Leu Phe Leu Thr Gly Pro Pro Ser Pro
                245                 250                 255

Tyr Asp Arg Leu His Val Trp Ser Gly Pro Gln Ala Leu Gln Arg Phe
            260                 265                 270

Leu His Asp Pro Thr Leu Thr Trp Ser Glu Leu Val Ala Ser Gly Lys
        275                 280                 285

Leu Arg Leu Asp Ser Pro Leu Lys Leu Gln Leu Leu Glu Asn Glu Trp
    290                 295                 300

Leu Ser Arg Leu Phe
305

<210> SEQ ID NO 9
<211> LENGTH: 25
<212> TYPE: DNA
<213> ORGANISM: Artificial
```

```
<220> FEATURE:
<223> OTHER INFORMATION: PCR Primer

<400> SEQUENCE: 9
agtctagagc tgacgtctct gtctg                                              25

<210> SEQ ID NO 10
<211> LENGTH: 29
<212> TYPE: DNA
<213> ORGANISM: Artificial
<220> FEATURE:
<223> OTHER INFORMATION: PCR Primer

<400> SEQUENCE: 10
acctcgagat ggcaagtgtt gttggttgg                                          29
```

VARIANT TAX GENE OF BOVINE LEUKEMIA VIRUS

BACKGROUND OF THE INVENTION

1. Field of the Invention

The present invention relates to a variant tax gene of bovine leukemia virus. The variant tax gene has enhancing ability to induce bovine leukemia virus replication.

2. Disclosure of the Related Art

Bovine leukemia virus (BLV) is a retrovirus most closely related to human T-cell leukemia virus (HTLV). Similar to human immunodeficiency virus (HIV), this virus has been known to have a gene that regulates viral replication and also tax gene that participates in transcription. The ratio of cattle infected by the virus (infection rate in Japan) is 10 to 20%, and 1 to 2% of the infected cattle develop extremely malignant enzootic bovine leukosis to die after a long latent period of about 10 to 15 years. Economic loss of stockbreeders caused by the virus is very serious, and accordingly, researches of the mechanism of the replication of BLV are highly important to develop means for preventing or treating infection caused by the virus.

SUMMARY OF THE INVENTION

The inventors of the present invention noted the fact that bovine individuals infected by BLV are classified into three characteristic pathological conditions, i.e., healthy individuals but positive to the antiviral antibody, those developing persistent lymphocytosis (PL) and those developing enzootic bovine leukosis, which is B lymphoma, after a long latent period, and the inventors made efforts to elucidate cause of the phenomenon at a genetic level. As a result, they found that various variants of the tax gene exist, and virus strains with a Tax protein including one or more particular mutations had enhanced transcription activity compared to wild-type virus strains.

The present inventors further continued researches, and found that mutations of the tax gene effected not only on the ability to activate the expression of the viral gene, but also on the strength of viral proliferation ability, and that viral strains having a particular variant tax gene had remarkably enhanced proliferation ability. The present invention was achieved on the basis of these findings.

The present invention thus provides a variant tax gene of bovine leukemia virus, which encodes a variant gene product containing one or more mutations selected from the group consisting of:
substitution of the 240th serine for threonine,
substitution of the 247th aspartic acid for glycine,
substitution of the 251st threonine for alanine,
substitution of the 258th aspartic acid for glycine,
substitution of the 261st histidine for arginine,
substitution of the 261st histidine for tyrosine, and
substitution of the 265th serine for glycine.

The present invention also provides a gene which contains the aforementioned variant tax gene and functions to enhance ability to induce replication of the bovine leukemia virus or a retrovirus related to the bovine leukemia virus (e.g., HTLV and HIV), preferably the bovine leukemia virus; and a gene which contains the aforementioned variant tax gene and functions to enhance ability to activate transcription of the bovine leukemia virus or a retrovirus related to the bovine leukemia virus, preferably the bovine leukemia virus.

According to another aspect of the present invention, there is provided a protein which is a product of a bovine leukemia virus tax gene and contains one or more mutations selected from the group consisting of:
substitution of the 240th serine for threonine,
substitution of the 247th aspartic acid for glycine,
substitution of the 251st threonine for alanine,
substitution of the 258th aspartic acid for glycine,
substitution of the 261st histidine for arginine,
substitution of the 261st histidine for tyrosine, and
substitution of the 265th serine for glycine.

The present invention also provides the aforementioned protein which enhances ability to induce replication of bovine leukemia virus or a retrovirus related to the bovine leukemia virus, preferably the bovine leukemia virus; and the aforementioned protein which enhances ability to activate transcription activity of bovine leukemia virus or a retrovirus related to the bovine leukemia virus, preferably the bovine leukemia virus.

According to preferred embodiments of the present invention, the aforementioned variant gene product is selected from those including substitution of the 240th amino acid, i.e., serine, for threonine, substitution of the 247th amino acid, i.e., aspartic acid, for glycine, or substitution of the 261st amino acid, i.e., histidine, for arginine. The gene of the present invention preferably encodes any one of the aforementioned preferred gene products.

According to another aspect of the present invention, there is provided a bovine leukemia virus having enhanced replication ability which contains the aforementioned gene. According to still another aspect of the present invention, there is provided a recombinant vector containing the aforementioned gene of the present invention which has enhancing ability to induce replication of bovine leukemia virus or a retrovirus related to the bovine leukemia virus, preferably the bovine leukemia virus.

According to still further aspects of the present invention, there are provided a method for producing a wild-type bovine leukemia virus, which comprises the steps of infecting a host cell introduced with a recombinant vector containing the aforementioned gene with a wild-type bovine leukemia virus, and culturing the resulting cell; and a method for enhancing ability to induce replication of bovine leukemia virus or a retrovirus related to the bovine leukemia virus, preferably a wild-type bovine leukemia virus, which comprises the step of expressing the aforementioned gene in a cell infected by the bovine leukemia virus or the retrovirus related to the bovine leukemia virus.

BRIEF EXPLANATION OF THE DRAWING

FIG. 1 depicts the amino acid sequence of the gene product of the wild-type tax gene, and amino acid sequences of gene products of variant tax genes that have high transcription-activating ability. The amino acids are shown as one letter symbols, and only the different amino acids are shown in the gene products of variant tax genes. The arrows indicate positions of substitution of amino acids.

BEST MODE FOR CARRYING OUT THE INVENTION

The tax gene of the bovine leukemia virus has already been known, and the full sequence is disclosed in Proc. Natl. Acad. Sci. USA, 81, pp.4741–4745, 1984. The genes of the present invention are variants of the tax gene, which encode variant gene products of the bovine leukemia virus tax gene that contain, in the product of the bovine leukemia virus tax gene, substitution of the 240th amino acid, i.e., serine, for threonine; substitution of the 247th amino acid, i.e., aspartic acid, for glycine; substitution of the 251st amino acid, i.e., threonine, for alanine; substitution of the 258th amino acid, i.e., aspartic acid, for glycine; substitution of the 261st amino acid, i.e., histidine, for arginine; substitution of the 261st amino acid, i.e., histidine, for tyrosine; or substitution of the 265th amino acid, i.e., serine, for glycine. The gene of the present invention may contain two or more of these mutations in combination.

The gene of the present invention may be either DNA or RNA. The gene of the present invention can readily be obtained by, for example, the PCR (polymerase chain reaction) utilizing suitable primers Specific examples of the preparation are explained in detail in examples of the specification. The gene product of the gene of the present invention can be produced by introducing a vector for gene expression that contains the gene of the present invention into a host cell, and culturing the resulting transformed cell. A type of the host cell is not particularly limited. For example, microbial cells such as *Escherichia coli*, yeast, insect cells, animal cells and the like can be used.

The gene of the present invention has a function to enhance ability to induce the replication of the bovine leukemia virus, and also a function to enhance ability to induce transcription activity of the bovine leukemia virus. These functions of the gene of the present invention can readily be verified according to the methods specifically explained in the examples of the specification. In addition, the gene of the present invention has a function to enhance ability to induce replication of retroviruses related to the bovine leukemia virus, for example, human immunodeficiency virus (HIV), and a function to enhance ability to induce the transcription activity of such retroviruses.

The gene of the present invention encompasses any modified gene which includes substitution, insertion, and/or deletion of one or several nucleotides and has function to enhance ability to induce the replication or transcription activity that is substantially similar to that of the aforementioned specified genes. The gene product of the present invention encompasses any protein which is encoded by the aforementioned specified gene or the aforementioned modified gene and functions to enhance ability to induce the replication or transcription activity for the bovine leukemia virus or retroviruses related thereto.

Such modified genes can be obtained by subjecting, for example, *Escherichia coli* cells having a wild-type gene to a treatment to cause mutations by using a reagent such as N-nitro-N'-nitro-N-nitrosoguanidine, and recovering genes encoding modified proteins from the cells. Gene products of the resulting genes can be produced by a conventional method for gene expression. In addition, deletion, substitution, or addition of nucleotides may be directly introduced by, for example, direct treatment of the gene of the present invention with a reagent such as sodium sulfite, or alternatively, by the site-specific mutagenesis (Kramer, W. et al., Methods in Enzymology, 154, 350, 1987), the recombinant PCR (PCR Technology, Stockton press, 1989) or the like. Whether or not a modified gene has the desired promoting activity on virus replication can be readily determined by the method described in the examples of the specification.

Although the mode of using the gene of the present invention is not particularly limited, the gene can be used in, for example, a method for producing a recombinant virus having enhanced replication ability which comprises the steps of removing the tax gene from the bovine leukemia virus, and then introducing the gene of the present invention as foreign gene; a method for increasing replication rate of the bovine leukemia virus which comprises the steps of incorporating the gene of the present invention into a vector for gene expression, and then introducing the resulting recombinant vector into a BLV-infected cell; a method for increasing replication rate of the wild-type virus which comprises the steps of introducing the resulting recombinant vector into various cultured cells to allow expression of gene products in the host cells, and infecting the host cells with a wild-type virus or the like. However, methods of using the gene of the present invention are not limited to those examples.

The gene of the present invention is useful for studies of the replication mechanism of the bovine leukemia virus and retroviruses related thereto. The gene is also useful for studies to establish a method for preventive and therapeutic treatment of bovine leukemia, and methods for preventive and therapeutic treatment of infectious diseases caused by retroviruses related to the bovine leukemia virus. In the same manner, the gene product of the gene of the present invention is useful for studies of the replication mechanism of the aforementioned viruses, and studies to establish methods for preventive and therapeutic treatment of the aforementioned diseases.

EXAMPLE

The present invention will be explained more specifically with reference to the following example. However, the scope of the present invention is not limited to the following example.

Example 1

Total DNA was extracted from three BLV-infected healthy cattle and three cattle developing leukemia. Full length tax genes were amplified by PCR by using each of the extracted DNA as a template, cloned in a conventional manner, and sequenced the full length nucleotide sequence of the tax genes derived from six cattle in total. The following primers were used as the PCR primers, and the reaction was performed by preincubation at 94° C. for 2 minutes, 35 cycles each comprised of incubations at 94° C. for 30 seconds, 60° C. for 30 seconds, and 72° C. for 1 minute and 30 seconds, and final incubation at 72° C. for 5 minutes.

Btax 2: 5' AG <u>TCT AGA</u> GCT GAC GTC TCT GTC TG 3' (SEQ. ID. NO. 9)
 (The underlined indicates the XbaI restriction site)
Btax 3: 5' AC <u>C TCG AGA</u> TGG CAA GTG TTG TTG GTT GG 3' (SEQ. ID. NO. 10)
 (The underlined indicates the XhoI limitation site)

The PCR products were digested by using restriction enzymes XhoI and XbaI, and thus digested fragments containing a variant tax gene were ligated to the XbaI and XhoI sites of high expression vector pME18Neo. The resulting vectors were co-transfected to 293T cells with a reporter vector pBLTR-Luc containing BLV Long terminal repeat (LTR) that was ligated upstream of luciferase gene in pGV-P vector (Toyo Ink Co., Ltd.) Luciferase analysis was performed by a conventional method (Virology, 243, pp.235–246, 1998).

As a result, remarkable differences in the transcription activating ability for BLV LTR were observed among the variant tax genes. Based on the strength of the activity, the variants were classified into three groups, i.e., 1) those substantially losing the transcription activity, 2) those having the transcription activity comparable to the wild-type gene, and 3) those having the transcription activity about 4 to 18 times higher than that observed with the wild-type gene. Nucleotide sequences of the variants were determined by an ordinary method and their deduced amino acid sequences were compared to each other. As a result, 7 variants containing an amino acid substitution were found among those exhibiting high transcription activity (FIG. 1; S240T, D247G, T251A, D258D, H261R, H261Y and S265G). The 7 variants were isolated and purified during sequencing, a process which one of ordinary skill in the art would understand and utilize. In Table 1, the transcription activating abilities were shown as relative values based on the ability of wild-type tax gene.

TABLE 1

| Tax gene | Transcription activating ability (relative value) |
| --- | --- |
| Control DNA | 0.06 |
| Wild-type tax | 1 |
| S240T | 10.05 |
| D247G | 17.91 |
| T251A | 7.38 |
| D258G | 3.67 |
| H261R | 16.64 |
| H261Y | 4.86 |
| S265G | 5.57 |

Then, expression vectors each containing S240T, D247G or H261R chosen from the variant genes exhibiting high transcription activating ability, a variant gene exhibiting low activity, or the wild-type tax were transiently transfected into AKATA cells which were stably introduced with BLV-infectious clone pBLF-IF (Virology, 245, pp.53–64, 1998). After 60 hours, Western blotting was performed in a conventional manner by using blood serum of BLV-infected sheep (Virology, 245, pp.53–64, 1998) and expression-inducing abilities for BLV structural proteins (gp30, p24, gp51, and Pr45Gag) in the transfected cells were compared among the wild-type, the low activity type, and the high activity type tax genes (Table 2). In the table, the amounts of protein expression are shown as numerical values representing the density of each band detected during the Western blotting by using Bio Image Analyzer. The high activity type tax genes exhibited 2 to 3.5 times higher expression-inducing abilities for BLV structural proteins than those of the wild-type tax gene.

TABLE 2

| | Introduced DNA | | | | | |
| --- | --- | --- | --- | --- | --- | --- |
| BLV Protein | Control DNA | Wild-type tax gene | Low Activity type tax gene | High Activity type tax gene | | |
| | | | | S240T | H261R | D247G |
| Pr45Gag | 0.34 (0.4) | 0.857 (1) | 0.309 (0.36) | 1.624 (1.89) | 2.533 (2.96) | 2.948 (3.44) |

TABLE 2-continued

| | Introduced DNA | | | | | |
| --- | --- | --- | --- | --- | --- | --- |
| BLV Protein | Control DNA | Wild-type tax gene | Low Activity type tax gene | High Activity type tax gene | | |
| | | | | S240T | H261R | D247G |
| gp30 | 0.467 (0.28) | 1.692 (1) | 0.45 (0.27) | 2.148 (1.27) | 2.707 (1.6) | 3.867 (2.29) |
| p24 | 0.718 (0.11) | 1.575 (1) | 0.217 (0.14) | 3.134 (1.99) | 3.525 (2.24) | 3.341 (2.12) |

Reverse transcriptase activity of BLV particles collected from culture supernatants of the cells transfected with the various genes was measured by a conventional method (Virology, 245; pp.53–64, 1998). Expression vectors comprising the wild type, the low activity type, or the high activity type tax gene, and the control vector were each transiently transfected into AKATA cells stably introduced with the BLV-infectious clone pBLF-IF. After 60 hours, the viruses in each culture supernatant was concentrated by ultracentrifugation, and the reverse transcriptase activity was measured as uptake of $^3$H-TTP by using poly(rT)-p(dT)$_{12-18}$ is as template (Table 3). In the table, the reverse transcriptase activities are shown as amounts of $^3$H-TTP uptake.

TABLE 3

| | Introduced DNA | | | | | |
| --- | --- | --- | --- | --- | --- | --- |
| | Control DNA | Wild-type tax gene | Low Activity type tax gene | High Activity type tax gene | | |
| | | | | S240T | H261R | D247G |
| reverse transcriptase activity | 320 | 1967 | 255 | 3179 | 2490 | 5251 |
| Relative value | 0.16 | 1 | 0.13 | 1.62 | 1.27 | 2.67 |

It was found that the high activity type tax genes enhanced the ability to produce the BLV particle by approximately 3 times as compared with the wild-type tax gene. Moreover, Western blotting analysis (Virology, 245, pp.53–64, 1998) of the virus particles revealed that the expression amount of structural proteins in BLV particles (gp30, p24, and gp51) obtained with the high activity type tax gene was 5 times higher than that obtained with the wild-type or the low activity type tax gene. As described above, the tax genes that exhibited high transcription-activating ability also increased the amount of viral production of the BLV and the expression of virus protein.

Furthermore, a molecular clone was prepared by replacing a portion of the wild-type tax gene of the BLV-infective molecular clone pBLV-IF, i.e., 727 base pairs from the ClaI cleavage site to the Eco47III cleavage site (from the 26th amino acid to the 271st amino acid), with the variant tax gene. By introducing the recombinant virus into a cell in the absence of the tax expression vector, the amount of virus production and expression of virus protein were increased compared to cells introduced with a wild-type infective molecular clone.

What is claimed:

1. An isolated and purified variant bovine leukemia virus tax gene, which encodes a variant gene product containing one or more mutations selected from the group consisting of:

substitution of the 240th serine for threonine,
substitution of the 247th aspartic acid for glycine,
substitution of the 251st threonine for alanine,
substitution of the 258th aspartic acid for glycine,
substitution of the 261st histidine for arginine,
substitution of the 261st histidine for tyrosine, and
substitution of the 265th serine for glycine.

* * * * *